United States Patent [19]

McNichols et al.

[11] Patent Number: 5,047,007

[45] Date of Patent: Sep. 10, 1991

[54] METHOD AND APPARATUS FOR PULSED IONTOPHORETIC DRUG DELIVERY

[75] Inventors: Larry A. McNichols, Coon Rapids; Gary A. Lattin, Forest Lake, both of Minn.

[73] Assignee: Medtronic, Inc., Minneapolis, Minn.

[21] Appl. No.: 456,013

[22] Filed: Dec. 22, 1989

[51] Int. Cl.$^5$ .............................................. A61N 1/30
[52] U.S. Cl. .................................... 604/20; 128/421; 128/898
[58] Field of Search ...... 604/20; 128/419 B, 421–422, 128/898

[56] References Cited

U.S. PATENT DOCUMENTS

| | | | |
|---|---|---|---|
| 3,794,910 | 2/1974 | Ninke et al. | 324/30 R |
| 3,991,755 | 11/1976 | Vernon et al. | 128/172.1 |
| 4,019,510 | 4/1977 | Ellis | 128/172.1 |
| 4,141,359 | 2/1979 | Jacobsen et al. | 128/172.1 |
| 4,149,533 | 4/1979 | Ishikawa et al. | 128/172.1 |
| 4,292,968 | 10/1981 | Ellis | 128/207.21 |
| 4,301,794 | 11/1981 | Tapper | 128/207.21 |
| 4,340,047 | 7/1982 | Tapper et al. | 128/207.21 |
| 4,406,658 | 9/1983 | Lattin et al. | 604/20 |
| 4,456,012 | 6/1984 | Lattin | 604/20 |
| 4,725,263 | 2/1988 | McNichols et al. | 604/20 |
| 4,764,164 | 8/1988 | Sasaki | 604/20 |
| 4,808,152 | 2/1989 | Sibalis | 604/20 |
| 4,846,950 | 7/1989 | Yao et al. | 604/20 |

FOREIGN PATENT DOCUMENTS

| | | |
|---|---|---|
| 0292930 | 5/1988 | European Pat. Off. . |
| 0309093 | 8/1988 | European Pat. Off. . |

OTHER PUBLICATIONS

Article Entitled "Studies on the Conducting Properties of the Human Skin to Direct Current", T. Rosendal, *Acta Physiologica*, vol. 5, pp. 130–151, 1943.
Article Entitled "The Current–Voltage Relationship in Human Skin", W. G. S. Stephens, *Med. Electron. Biol. Engng.*, vol. 1, pp. 389–399, 1963.
Article Entitled "Square-Wave Analysis of Skin Impedance", D. T. Lykken, *Psychophysiology*, vol. 7, No. 2, pp. 262–275, 1971.
Article Entitled "Skin Resistance During Square-Wave Electrical Pulses of 1 to 10 mA", A. Van Boxtel, *Med. & Biol. Eng. & Comput.*, vol. 15, pp. 679–687, Nov. 1977.
Article Entitled "Transdermal Iontophoretic Delivery of Therapeutic Peptides/Proteins", Y. W. Chien et al., *Annals New York Academy of Sciences*, pp. 32–51, 1987.
Article Entitled "New Ionotophoretic Transdermal Administration of the Beta–Blocker Metoprolol", K. Okabe et al., *J. Controlled Release*, vol. 4, pp. 79–85, 1986.
Article Entitled "Formative Mechanisms of Current Concentration and Breakdown Phenomena Dependent on Direct Current Flow Through the Skin by a Dry Electrode", T. Yamamoto et al., *IEEE Transactions of Biomedical Engineering*, vol. BME-33, No. 4, pp. 396–404, Apr., 1986.
Article Entitled "Iontophoresis in Dermatology: A Review", J. B. Sloan et al., *J. Am. Acad. Dermatol.*, vol. 1, pp. 671–684, 1986.
Article Entitled "Iontophoretic Delivery of Drugs: Fundamentals, Developments, and Biomedical Applications", A. K. Banga et al., *J. Controlled Release*, vol. 7, pp. 1–24, 1988.
Article Entitled "A Comparison of Pulsed and Continuous Current Iontophoresis", T. Bagniefski et al., *J. Controlled Release*, vol. 11, N1-3, pp. 113–122, 1990.

*Primary Examiner*—Stephen C. Pellegrino
*Assistant Examiner*—Steven J. Shumaker
*Attorney, Agent, or Firm*—John A. Rissman; Daniel W. Latham

[57] ABSTRACT

A method and apparatus are disclose for transdermal iontophoretic delivery of ionic species, such as a drug in ionic form, in which therapeutic, electrical pulses having controlled, distinctive, dual-segment waveform characteristics are applied which facilitate more efficient drug administration throughout each pulse. The therapeutic pulses are generated at a predetermined frequency and have a predetermined pulse width. A first pulse segment and a second pulse segment comprise each dual-segment, therapeutic pulse. The electrical attributes of each pulse segment, including amplitude and duration, are controlled to produce the desired, pulsed output waveform.

16 Claims, 4 Drawing Sheets

METHOD AND APPARATUS FOR PULSED IONTOPHORETIC DRUG DELIVERY

BACKGROUND OF THE INVENTION

1. Field of the Invention

The present invention, in general, relates to the field of iontophoresis. In particular, the present invention relates to a method and apparatus for transdermal iontophoretic delivery of ionic substances by application of pulsed electrical energy having distinctive, complex waveform characteristics. These waveform characteristics are controlled to provide dual-segment, therapeutic pulses which significantly improve the efficiency of such iontophoretic treatment, without substantially increasing skin irritation.

2. Description of the Prior Art

Iontophoresis is a process which involves the transport of ionic substances into body tissue, such as through the skin, by the passage of a direct electric current through an electrolyte solution containing the ionic substance to be administered. Conventional iontophoretic devices typically include a battery and simple current control circuitry coupled to two electrodes, namely the active and indifferent electrodes. The active electrode contains the desired ionic substance to be administered, e.g., a drug in its ionic form having the same charge as the active electrode. The indifferent electrode is typically moistened with saline solution or provided with some other ionic conductive medium. The indifferent electrode serves as a ground electrode to close the electrical circuit through the body.

Iontophoresis offers many advantages to other conventional drug delivery regimens, such as oral administration by pills or intravenous administration by needle injection. In comparison to needle injection, for example, iontophoresis provides a noninvasive procedure with reduced trauma, pain, anxiety and risk of infection. Iontophoresis is well-adapted for local or topical treatment, such that high local concentration of the drug administered can be accomplished with a corresponding reduction of unwanted systemic side effects. Iontophoresis also offers great flexibility as to the rate of drug administration, regardless of whether the desired therapy is local or systemic, since the rate of drug delivery can be controllably varied by miniaturized programmable circuitry which precisely varies the iontophoretic current applied. Iontophoresis has been used, for example, for transdermal delivery of various drugs such as lidocaine hydrochloride, hydrocortisone derivatives, acetic acid, fluoride, penicillin, and dexamethasone sodium phosphate. It has also been used to deliver pilocarpine nitrate as part of a screening procedure for cystic fibrosis.

While the technique of iontophoretic drug delivery has been used clinically in delivering medication to surface tissues for several decades, the need for improving the efficiency of drug delivery and for reducing the risk of skin burns and general tissue irritation often associated with such therapy has limited its expanded use. The interplay of a multitude of chemical, electrical and physiological factors, which are known to influence iontophoretic drug delivery, present a complex background against which solutions to these problems have been made anything but obvious.

Some of these factors which must be managed include, for example: (a) various electrochemical factors, such as the type, molecular size, weight and ionic concentration of the drug, presence of extraneous ions competing with the charged drug molecules, and pH conditions at the interface of the skin and active electrode; (b) various electronic factors associated with active transport of the charged drug, such as the power source voltage, the type and surface area of the electrodes, use of constant or pulsed DC current, pulse width, and frequency; and (c) various physiological considerations peculiar to treatment of skin tissue, such as its permeability and sensitivity to each particular drug type, as well as the electrical properties of skin tissue. Further complexity arises from the fact that many of these factors can vary from patient to patient, and even as to the same patient as a function of specific body location receiving therapy, duration of therapy or therapeutic drug type.

Various approaches have heretofore been taken toward improving upon the management of the electronic-related factors identified above, but limited drug delivery efficiency has been obtained. It is management of these various electronic-related factors, and more particularly, an improved method and apparatus for more effectively accommodating the electrical properties presented by the skin tissue receiving pulsed iontophoretic drug therapy, to which the present invention is directed.

Since the quantity of ions transferred in an iontophoretic application is directly proportional to the current flow and its duration, conventional iontophoretic devices regulate drug dosage delivery by controlling current flow through the electrodes. Iontophoretic devices are disclosed, for example, with various current regulation schemes in the following patents:

| U.S. Pat. Nos. | Inventor |
| --- | --- |
| 3,794,910 | Ninke et al. |
| 3,991,755 | Vernon et al. |
| 4,019,510 | Ellis |
| 4,141,359 | Jacobsen et al. |
| 4,149,533 | Ishikawa et al. |
| 4,292,968 | Ellis |
| 4,301,794 | Tapper |
| 4,340,047 | Tapper et al. |
| 4,406,658 | Lattin et al. |
| 4,725,263 | McNichols et al. |
| 4,764,164 | Sasaki |
| 4,808,152 | Sibalis |
| Foreign Pat. Nos. | |
| EP 0 292 930 A1 | Sibalis |
| EP 0 309 093 A1 | Masaki |

Prior art iontophoresis devices provide either a constant DC or a pulsed DC current to drive the electrodes. Unfortunately, using either mode of operation has required a tradeoff between drug delivery efficiency and irritation to the skin being treated. Over the same period of operation and peak current amplitude, for example, the constant DC mode will deliver greater quantities of drug than the pulsed DC mode, primarily due to the constant DC mode's uninterrupted current flow (i.e., the effective duration of current flow, or the effective average current, is greater). Associated with the constant DC mode, however, there is a constant polarizing current producing a residual charge within the body tissue, which is at least partially depolarized when operating in the pulsed DC mode during the "off" time interval between pulses. Consequently, the constant DC mode tends to produce greater irritation to the skin beneath the electrode than that caused when using the pulsed DC mode.

Thus, a primary challenge to those skilled in this art over recent years has been to develop techniques for improving the drug delivery efficiency of the pulsed iontophoretic modality without compromising its desirably low skin irritation benefits.

The approaches which the prior art has taken toward further reducing skin irritation and improving the drug delivery efficiency of devices which operate in the pulsed DC mode relate to methods for reducing the residual charge within the body tissue by actively assisting the depolarization function in between therapeutic pulses. U.S. Pat. Nos. 4,301,794 (Tapper) and 4,340,047 (Tapper et al.), for example, teach periodically interrupting a unidirectional treatment current (FIG. 1, treatment current 14 of waveform 12) with a relatively short pulse of current in the opposite direction (pulse 16). U.S. Pat. No. 4,764,164 (Sasaki) also discusses the use of forced-discharge type reverse pulses between therapeutic pulses, as well as the use of a switch mechanism (e.g., FIG. 3, switch 7) coupled in parallel to the skin electrodes to affect depolarization by short-circuit discharge between therapeutic pulses.

Even with these approaches, however, the drug delivery efficiency of iontophoretic devices operating in the pulsed DC mode has not been entirely adequate and a need for significant improvement has continued. As will become apparent from the following, the present invention satisfies that need.

SUMMARY OF THE INVENTION

The present invention is embodied in a method and apparatus for pulsed iontophoretic drug delivery, and more particularly, the specific manner in which the waveforms of such therapeutic pulses are generated. The method and apparatus comprise specific improvements to conventional pulsed iontophoretic drug therapy.

The present invention provides a novel iontophoretic therapy, wherein pulsed electrical energy having distinctive, complex waveform characteristics is generated and applied to facilitate more efficient administration of the drug throughout each therapeutic pulse, without substantially increasing skin irritation.

In accordance with the present invention, a train of periodic electrical pulses having a predetermined frequency and a predetermined pulse width are generated, the waveform characteristics of each pulse thereof being controlled to provide a dual-segment pulse waveform. Each dual-segment, therapeutic pulse thus generated is comprised of a first pulse segment and a second pulse segment, each segment of which has a controlled duration and amplitude. The first pulse segment extends over a predetermined first portion of the pulse width, such first portion comprising not more than 50% of the pulse width. The second pulse segment extends over a subsequent second portion which comprises the remaining portion of the pulse width.

The electrical attributes of each pulse segment are selected to provide a unidirectional iontophoretic current throughout each therapeutic pulse. More particularly, the electrical attributes of each pulse segment are controlled to deliver periodic electrical energy which more effectively interacts with the electrochemically-induced impedance of the skin tissue being treated throughout each pulse. A primary function of the first pulse segment is to rapidly charge the capacitive component of the skin during an initial portion of each therapeutic pulse. As a result thereof, the desired iontophoretic current flow and associated ion transport through skin tissue can be affected over a greater proportion of each therapeutic pulse, which is a primary function of the second pulse segment of each therapeutic pulse.

In one aspect of this invention, an apparatus is disclosed for generating alternative types of the dual-segment, therapeutic pulse, namely either voltage-plus-current pulse segments or current-plus-current pulse segments. In the type wherein each dual-segment, therapeutic pulse, is comprised of voltage-plus-current pulse segments, the first pulse segment comprises a voltage output having a predetermined or controlled average voltage amplitude and the second pulse segment comprises a current output having a predetermined or controlled average current amplitude. In the type wherein each dual-segment, therapeutic pulse is comprised of current-plus-current pulse segments, the first pulse segment comprises a current output having a predetermined or controlled first average current amplitude and the second pulse segment comprises a current output having a predetermined or controlled second average current amplitude, wherein the first average current amplitude is greater than the second average current amplitude.

In another aspect of this invention, an apparatus is disclosed for generating a dual-segment, voltage-plus-current, therapeutic pulse, such embodiment also having a sensor-feedback means for sensing an electrode potential during application of each pulse, wherein sensor-feedback means also includes means for feedback of a signal representative of the potential sensed and for controlling the pulse waveform as a function of the feedback signal.

DETAILED DESCRIPTION OF THE INVENTION

To better understand the operation of the present invention, it is necessary to consider the electrochemical factors interacting with biological tissue being treated iontophoretically. Human skin is a complex, non-homogeneous membrane comprised of several skin tissue layers which extend inwardly from the outside skin surface and comprise stratum corneum, epidermis, dermis and subdermal tissue, depending upon the iontophoretic penetration obtained. Skin being iontophoretically treated is known to possess electrical properties which include both resistive and capacitive characteristics which cooperatively present an electrical impedance tending to oppose the desired iontophoretic current flow during pulsed therapy. These electrical properties are understood to be dominated by the stratum corneum. The stratum corneum consists of multilayers of horny cells which possess relatively low water content and thus serves as a relatively good insulator. As such, a substantial percentage of the overall skin impedance is attributable to the stratum corneum.

This skin impedance phenomena associated with transdermal iontophoretic drug therapy has received increased study and experimentation over recent years. It is known, for example, that the application of an electrical field across biological tissue during conventional iontophoretic drug therapy, regardless of whether the iontophoretic current is delivered using constant or pulsed DC modality, induces unwanted electrochemical polarization that tends to oppose and diminish or prevent continued migration of ionic substances in the desired direction through the skin tissue, and also tends to produce skin irritation. It is also known that the delivery of iontophoretic current in a periodic or pulsed DC mode tends to reduce skin irritation associated with such therapy, but at the expense of reduced drug delivery rates. Experimentation involving the use of various types of periodic waveforms, such as sinusoidal, trapezoidal, square, or rectangular input current waveforms, also suggests that square or rectangular waveforms tend to provide greater drug delivery efficiency over extended periods of iontophoretic therapy. While numerous theoretical models which derive from the Nernst-Plank equation have been proposed to explain the electrochemical mechanisms which relate this skin impedance phenomena with the particular pulse modality being used, none of these theories have been entirely successful in correlating the theoretical predictions and the experimental observations associated with prior research in this area.

Figure 1:
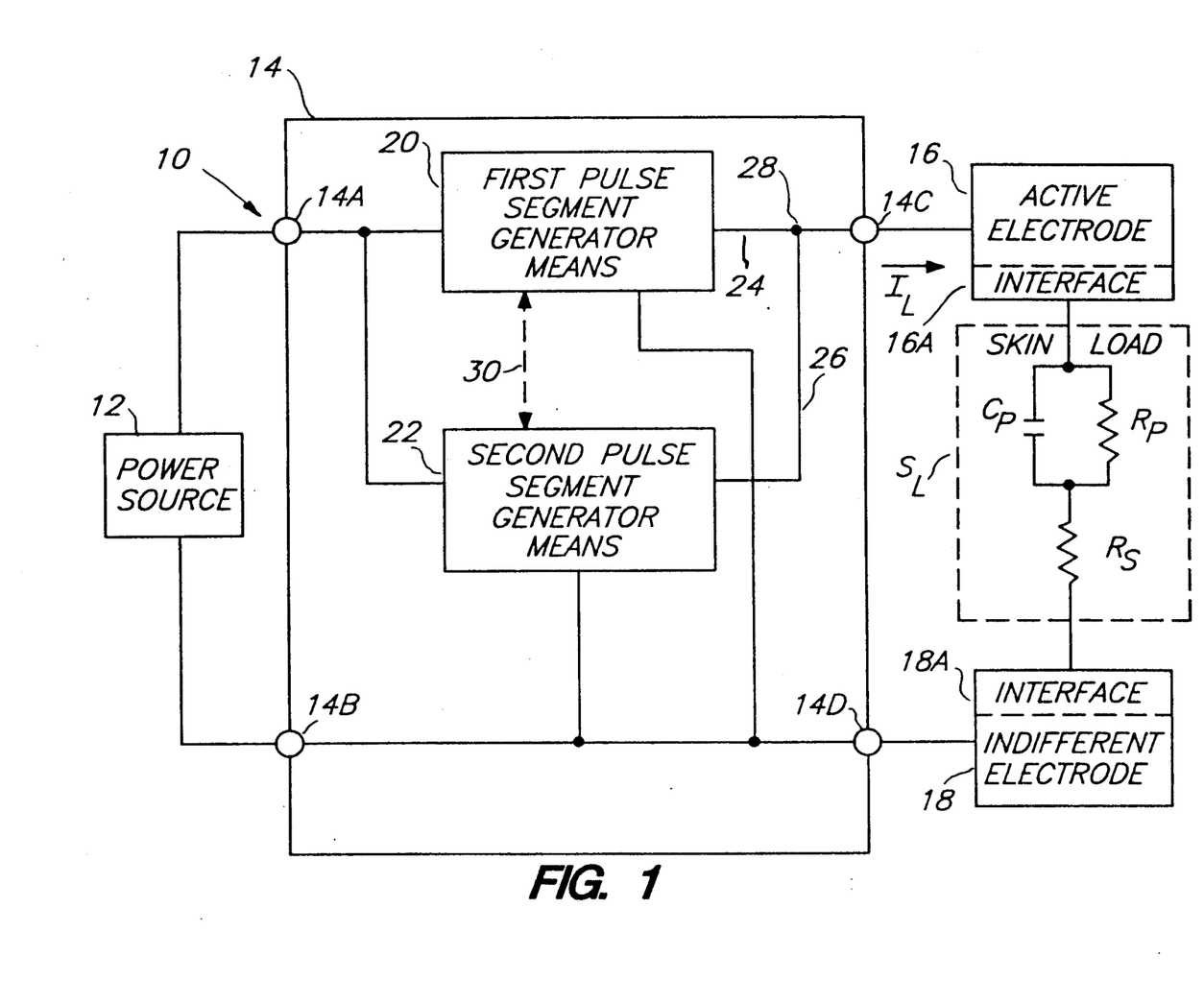
FIG. 1 is a block diagram representation of a preferred embodiment of the invention for providing dual-segment, therapeutic pulses, showing the present iontophoresis device coupled to a skin load which is illustrated by a simplified equivalent electrical model for skin tissue.

A generally accepted, highly simplified prior art electrical model equivalent of intact human skin is schematically illustrated in FIG. 1, indicated generally as skin load $S_L$. Skin load $S_L$ is a reactive circuit comprising a parallel connection of a resistance component $R_P$ and a capacitance component $C_P$ which parallel connection is in series with resistance component $R_S$. While somewhat oversimplified, skin load $S_L$ is roughly analogous to the skin tissue components described above as follows: series resistance component $R_S$ represents an ohmic resistance component of the various skin tissue layers in the iontophoretic current path, parallel resistance component $R_P$ represents a leakage or shunt resistance component of the stratum corneum, and parallel capacitance component $C_P$ represents a capacitive component of the stratum corneum.

While nominal differences from the simplified equivalent electrical skin model shown as skin load $S_L$ do exist among the prior art, including the relative quantitative electrical values which may be assigned to each electrical component thereof, the generalizations embodied in modeled skin load $S_L$ remain valid for purposes of broadly illustrating the electrical response of the skin to applied pulsed waveforms. It is noted, however, that certain equivalent electrical components associated with skin load $S_L$, such as those relating to the skin-electrode interface, have not been schematically illustrated, since the same are not believed pertinent to understanding the skin impedance phenomena to be discussed herein. It is also noted that the electrical properties of human skin are known to vary not only from person to person, but these electrical properties may also vary as to the same person. Such variations can occur, for example, depending upon the specific body location receiving iontophoretic therapy, in response to the type of drug used, in response to the type of pulsed waveform used, and over the duration of the therapy.

The specific electrical components of skin load $S_L$ can be characterized as follows: $R_S$ is a resistance component with values ranging between 50 to 500 ohms, one-third of which is believed to reside in the laminae of the stratum corneum; $C_P$ is a capacitive component corresponding to a polarization capacity of skin $S_L$, with values ranging between 0.01 to 0.10 microfarads, the majority of which is attributable to the stratum corneum; and $R_P$ is a resistive component with values ranging between 3,000 and 40,000 ohms, the majority of which is attributable to the stratum corneum, although $R_P$ will also vary considerably as a function of the size and type of material used for the electrodes. Thus, it appears that the main determinants of skin impedance, particularly parallel components $C_P$ and $R_P$, reside more superficially in the skin, mainly that of the stratum corneum. As to variability of these components for each individual, $R_S$ and $C_P$ remain relatively constant values, while $R_P$ varies non-linearly with current intensity. With respect to pulsed waveforms, such as square or rectangular waveforms, the skin impedance is known to decrease with increases in pulse frequency. As to component variability from person to person, the most significant is $R_P$, which varies by a factor of 2 to 14.

For purposes of briefly explaining the significance of the skin impedance phenomena, a general description of the electrical response of skin load $S_L$ when coupled to a conventional iontophoretic drug delivery device which produces rectangular-wave, current pulse waveforms is believed helpful. For this example, it is assumed that the desired effects of reduced skin irritation by actively causing partial or complete depolarization of the skin tissue between therapeutic pulses is accomplished in a conventional manner, such as by applying reverse polarity current or short-circuiting the electrodes during some portion of the interval between therapeutic pulses.

During each therapeutic pulse, skin load $S_L$ presents a total impedance comprised of a resistance, consisting of $R_P$ and $R_S$, and a capacitive reactance which varies inversely with $C_P$ and the pulse frequency, which impedance opposes the desired iontopho-retic current flow. During each therapeutic pulse, it is necessary that $C_P$ recharges. The time properties of charging depend upon numerous factors, including amplitude of the applied iontophoretic current, individual values of the electrical components $R_P$, $C_P$ and $R_S$ which comprise a charging network having series and parallel RC elements, and the residual voltage or skin polarization present in skin load $S_L$.

The iontophoretic current flow established through $R_P$ of skin load $S_L$ is directly proportional to the desired rate of ion transport into the skin tissue being treated. It can be seen, however, that the parallel connection of $R_P$ and $C_P$ provides a dual pathway for the iontophoretic current. It is thus believed that the iontophoretic current which flows through such parallel connection is proportioned between each branch thereof, such that a portion of iontophoretic current which flows through $R_P$ varies in approximate inverse exponential proportion with that charging $C_P$. Accordingly, the amount of current flow which can be obtained through $R_P$ during each therapeutic pulse, and thus the quantity of ionic drug which can be delivered over each pulse, is inversely proportional to the time required in each pulse to charge $C_P$.

Having recognized this relationship, a primary objective of the present invention is to increase the quantity of ionic drug being delivered transdermally throughout each therapeutic pulse by reducing the charging time of the capacitive component of the skin $C_P$ during the initial portion of each therapeutic pulse. A particular type of periodic electrical energy is applied according to the present invention such that each therapeutic pulse is comprised of a first pulse segment and a second pulse segment, each segment of which has controlled electrical attributes such as duration and amplitude. This rapid charging of the skin's capacitive component $C_P$ constitutes a primary function of the first pulse segment of each therapeutic pulse. By so doing, the desired iontophoretic current flow and associated ion transport through skin tissue occurs over a greater proportion of each therapeutic pulse, which is a primary function of the second pulse segment of each therapeutic pulse. While the specific interplay of various chemical, electrical, and physiological factors involved in the iontophoretic therapy of the present invention is complex and not entirely understood, it appears that the use of this dual-segment, pulse waveform according to the present invention more effectively accommodates the particular electrical properties of skin tissue, thereby improving drug delivery efficiency.

In FIG. 1, a block diagram representation of a preferred embodiment of the invention is indicated generally at 10, illustrating an apparatus for providing dual-segment, therapeutic pulses to iontophoretically deliver an ionic species, such as a drug in ionic form, or any other type of charged substance to be administered.

Apparatus 10 comprises an electric power source 12, a pulse generator means 14 for generating a train of periodic pulses having a predetermined frequency, wherein each pulse has a predetermined pulse width as a function of the frequency (i.e., duty cycle) and a dual-segment pulse waveform according to the present invention as more fully described below, an active electrode 16 having an ionic drug to be delivered, and an indifferent electrode 18. Electrodes 16 and 18 are shown in electrical contact with a skin load $S_L$ at skin-electrode interface locations 16A and 18A, wherein skin load $S_L$ has been schematically illustrated by a simplified equivalent electrical model of skin tissue to receive iontophoretic therapy. Pulse generator means 14 further comprises input terminals 14a and 14b electrically coupled to power source 12 to energize pulse generator means 14, and output terminals 14c and 14d electrically coupled to electrodes 16 and 18 to deliver iontophoretic current to skin load $S_L$. Electrodes 16 and 18 are of conventional design preferably adapted to provide uniform current density to skin load $S_L$ tissue in contact therewith.

Apparatus 10 preferably comprises a small, light-weight, portable iontophoresis device suitable for use in direct adhesion application to the human skin to permit patient mobility. It should be understood, however, that it is the unique output of apparatus 10, namely, the dual-segment, therapeutic pulsed waveform, which constitutes a significant feature of the present invention. The features which are associated with the preferred embodiment of apparatus 10, namely, reduced size, reduced weight, portability, and reduced cost, comprise advantages of a secondary nature to that of the desired pulse waveform produced by the device. To achieve these advantages, however, power source 12 can comprise a light-weight, button-type, dry element battery, pulse generator means 14 can comprise circuitry which is primarily digital and can be readily fabricated as a custom integrated circuit at low cost and reduced size, and electrodes 16 and 18 can comprise conventional, slim, light-weight pads which adapt to skin surface contours and also provide support for power source 12 and pulse generator means 14.

Pulse generator means 14 generates a train of periodic electrical pulses having a predetermined frequency ranging between 0.5 kHz and 50 kHz and a predetermined pulse width ranging between 10% and 80% of each cycle period, the waveform characteristics of each pulse thereof being controlled to provide a distinctive, dual-segment, therapeutic pulse waveform which is more fully described below. A pulse interval separates each pulse from a subsequent pulse in the pulse train, and the electrical attributes of each pulse interval, are controlled to facilitate depolarization in the skin tissue and thereby reduce skin irritation in accordance with conventional practice.

Pulse generator means 14 further comprises a first pulse segment generator means 20 for generating a first pulse segment of the dual-segment therapeutic pulse, and a second pulse segment generator means 22 for generating a second pulse segment of the dual-segment therapeutic pulse. The first pulse segment extends over a predetermined first portion of the pulse width, such first portion comprising not more than 50% of the pulse width. The second pulse segment extends over a subsequent second portion which comprises the remainder of the pulse width. It should be understood, however, that the second pulse segment may be generated such that it is co-extensive with all, some or none of the first pulse segment, provided that at least some part of the second pulse segment, which constitutes the subsequent second portion of the pulse width, follows the first pulse segment.

According to the present invention, each dual-segment, therapeutic pulse generated by pulse generator means 14 can comprise voltage-plus-current pulses, or current-plus-current pulses, as desired. The iontophoretic current delivered to skin load $S_L$ using the present invention is unidirectional throughout each therapeutic pulse, such iontophoretic current shown generally at arrow $I_L$.

In the voltage-plus-current embodiment, first pulse generator means 20 provides a voltage output having a predetermined or controlled average amplitude ranging between 3 and 25 volts, and second pulse segment generator means 22 provides a current output having a predetermined or controlled average amplitude ranging between 0.01 and 5 milliamperes. A voltage output can be generated by a conventional voltage source having an output impedance which is low relative to that of the skin load impedance. A current output can be generated by a conventional current source having an output impedance which is high relative to that of the skin load impedance. Pulse generator means 14 preferably includes means for limiting the voltage amplitude and current amplitude of the pulsed output being delivered to skin load $S_L$, which can comprise conventional voltage clamping and current limiting circuitry interconnected in a known manner.

In the current-plus-current embodiment, first pulse generator means 20 provides a current output having a predetermined or controlled first average amplitude ranging between 0.1 and 50 milliamperes, and second pulse segment generator means 22 provides a current output having a predetermined or controlled second average amplitude ranging between 0.01 and 5 milliamperes, wherein the first average current amplitude is greater than the second average current amplitude. The output of first pulse segment generator means 20 is coupled to output terminal 14c along a line 24. The output of second pulse segment generator means 22 is coupled to output terminal 14c along a line 26 to line 24 via summing node 28.

As will be readily apparent to those skilled in the art, the present invention is capable of being practiced using a variety of circuit alternatives, comprised of conventional electronic components, adapted to generate a dual-segment, therapeutic pulse waveform to accomplish the above-described functions of rapid skin capacitance charging, and improved iontophoretic current flow. If desired, pulse generator means 14 can include means for automatically adjusting to changing conditions in load conditions in order that a desired iontophoretic current flow is maintained. For example, pulse generator means 14 can include a sensor-feedback means for sensing a parameter representative of iontophoretic current flow through the skin load $S_L$, such as voltage, current, or impedance, including means for feedback of a signal representative of the parameter sensed and for controlling the electrical attributes of the dual-segment pulse waveform, such as pulse frequency, pulse width, and amplitude or relative duration of each pulse segment, as a function of the feedback so that the desired drug delivery rate is maintained.

There is flexibility with respect to circuitry design to generate the desired periodic or pulse waveform. For example, first pulse segment generator means 20 and second pulse segment generator means 22 can comprise separate pulse generating circuit components for generating independent oscillating output, wherein pulse generator means 14 includes means for synchronizing their outputs to produce the desired dual-segment pulse waveform, such as by timing and gating circuitry. Alternatively, pulse generator means 14 can comprise a single pulse generator component, such as conventional oscillator means for providing an oscillating signal, wherein the oscillating signal enables output gates through which the respective outputs of first pulse segment generator means 20 and second pulse segment generator means 22 are coupled to the skin load in desired timed relation, thereby producing the desired dual-segment, therapeutic pulse.

There is further flexibility with respect to circuitry design to generate the desired pulse segments. If desired, for example, first pulse segment generator means 20 and second pulse segment generator means 22 can be interactively coupled as indicated generally by dashed line 30, to coordinate the relative timing of their respective output such that there may or may not be an overlap thereof. In other words, the second pulse segment may be generated by second pulse segment generator means 22 such that it is co-extensive with all, some or none of the first pulse segment. For example, the output of pulse generator means 14 can comprise a dual-segment, voltage-plus-current, therapeutic pulse, wherein the second pulse segment which comprises a current output extends throughout the entire pulse width, such that the current output is superimposed upon the first pulse segment which comprises a voltage output. Alternatively, second pulse segment generator means 22 can be controlled to initiate its output immediately upon the termination of the output of first pulse segment generator means 20, such that the second pulse segment does not overlap with the first pulse segment but is merely subsequent thereto. Partial overlap between the second pulse segment and a trailing portion of the first pulse segment is also possible. It should be apparent that the duration of each pulse segment can be determined by various threshold detection circuitry, wherein the operation of first pulse segment generator means 20 and second pulse segment generator means 22 is controlled in response to parameters such as timing, voltage, current, impedance, and the like.

Similar flexibility is available with respect to generating a dual-segment, therapeutic pulse comprised of current-plus-current pulse segments. An example of simplified circuitry design for generating a dual-segment, current-plus-current, therapeutic pulse follows. Pulse generator means 14 can comprise a single voltage source of conventional design adapted to provide rectangular-wave, pulsed voltage output of predetermined amplitude, frequency and pulse width. Pulse generator means 14 further comprises switching circuitry of conventional design which, couples the voltage output to output terminals 14c and 14d. The switching circuitry includes at least two circuit branches, each of which provide a pathway for current flow between the voltage source and output terminals 14c and 14d during each voltage pulse. A first circuit branch includes a selected first resistance and a second circuit branch includes a selected second resistance, wherein the resistances are selectively controlled such that the first resistance is less than the second resistance. The switching circuitry includes timing circuitry of conventional design which alternately couples the voltage output between the first circuit branch and the second circuit branch by switching between the branches according to a desired sequence and duration. The pulse generator means 14 thus provides a dual-segment, pulsed current output having an amplitude which varies between a predetermined first average current amplitude, which is a function of the amplitude of the voltage pulse and the first resistance, and a predetermined second average current amplitude, which is a function of the amplitude of the voltage pulse and the second resistance, such that the first current amplitude is greater than the second current amplitude.

There is further flexibility with respect to the type of periodic waveform which pulse generator means 14 can generate according to the present invention. While the particular waveform of each pulse segment is preferably rectangular or square-shaped, the waveform is not essentially limited to such type, and may comprise, for example, trapezoidal, ramped, or exponential waveforms.

Figure 2:
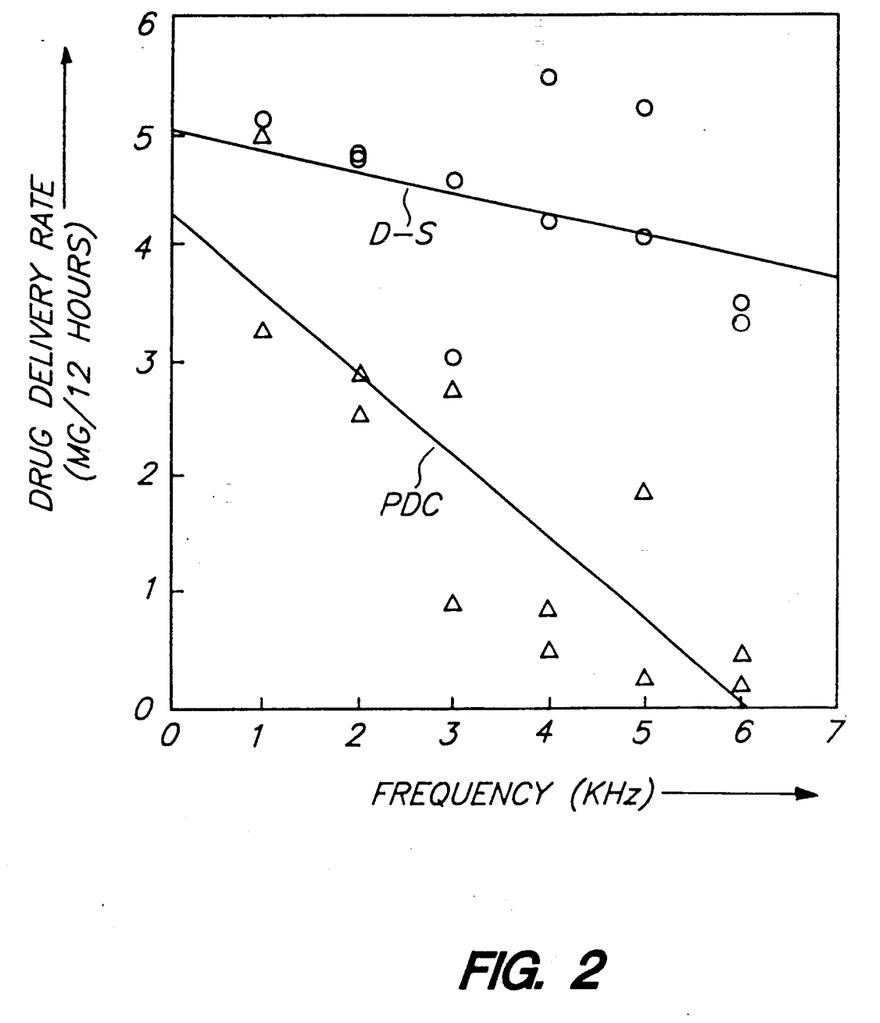
FIG. 2 is a graph illustrating drug delivery rates obtained using two different modalities of pulsed iontophoretic drug delivery, namely, a conventional, pulsed DC waveform and a dual-segment, voltage-plus-current, pulsed waveform according to the present invention, wherein comparative test results are graphed for each modality showing drug delivery efficiency as a function of pulse frequency.

Comparative test results which were obtained using two different modalities of pulsed iontophoretic drug delivery, namely, a conventional pulsed DC current ("Pulsed DC") and the dual-segment, voltage-plus-current, pulsed iontophoretic therapy of the present invention ("Dual-Segment") are graphed in FIG. 2. Data points corresponding to test results obtained using each modality have been graphed which indicate drug delivery efficiency as a function of pulse frequency. An overall test performance line has been drawn for each modality, which constitutes a "best fit" line based upon the individual data points obtained for each modality, as indicated at a line "PDC" corresponding to "Pulsed DC" and at a line "D-S" corresponding to "Dual-Segment".

The test conditions were as follows. The drug, hydromorphone hydrochloride, was iontophoretically administered to four weanling pigs weighing approximately 10 kilograms under controlled, equivalent environmental conditions over a two-day study. Iontophoretic devices were used which provided a pulsed output according to the "Pulsed DC" and "Dual-Segment" modalities. The pulsed output for each modality was tested over six different pulse frequencies, namely, test frequencies of 1 KHz, 2 KHz, 3 KHz, 4 KHz, 5 KHz and 6 KHz. The duty cycle for each test frequency was 50%.

A conventional, pulsed DC current output was delivered under the "Pulsed DC" modality, each current pulse thereof comprising a rectangular-type waveform having a substantially constant amplitude of 0.6 milliamperes. A dual-segment, voltage-plus-current, pulsed output was delivered under the "Dual-Segment" modality according to the present invention. Each "Dual-Segment" pulse consisted of a first pulse segment comprising a voltage output having a substantially constant amplitude of 24 volts, and a second pulse segment comprising a current output having a substantially constant amplitude of 0.6 milliamperes. The first pulse segment commenced at the beginning of each pulse, having a fixed duration of 1 microsecond regardless of the pulse width associated with the operating frequency used. The second pulse segment also commenced at the beginning of each pulse, having a variable duration such that the second pulse segment extended over the entire pulse width associated with the operating frequency used. Both pulse segments comprised a rectangular-type waveform.

Iontophoretic devices driving skin electrodes located on the dorsal aspect of each pig were operated continuously over a twelve-hour period using each modality. Each modality was tested on two pigs for each test frequency, each modality using a different pair of pigs. Thus, four separate data points are graphed for each test frequency in FIG. 2, which correspond to drug delivery measurements taken on each of the four pigs.

Conventional, circular-shaped, gel-type, iontophoresis electrodes, having a patch surface area of approximately 2 cm², were used. The active electrode and indifferent electrode were disposed in an electrode housing available from Medtronic, Inc. as Electrode Housing Model No. 6462. The active electrode consisted of a gel formulation comprised of purified water (88%), polyvinyl alcohol "PVA" (8%), hydroxypropylmethylcellulose "HPMC" (2%), and hydromorphone hydrochloride (2%). The indifferent electrode consisted of a gel formulation available from Medtronic, Inc. as Gel Model No. 6467 INA. This gel formulation is comprised of HPMC (4%), PVA (6%), glycerol (10%), purified water (79.01%), sodium chloride (0.9%), potassium chloride (0.04%), and hydrated calcium chloride ($CaCl_2$) (0.05%). The quantity of drug delivered was determined by measuring the residual drug remaining on the active electrode using conventional techniques including high pressure liquid chromatography.

From a comparison of the two test performance lines plotted in FIG. 2, it is clear that the drug delivery rates obtained using the "Dual-Segment" modality are significantly greater than those obtained using the conventional "Pulsed DC" modality. In particular, it can be seen that the differential between drug delivery rates for each modality increases as a function of increased operating frequencies.

Figure 3:
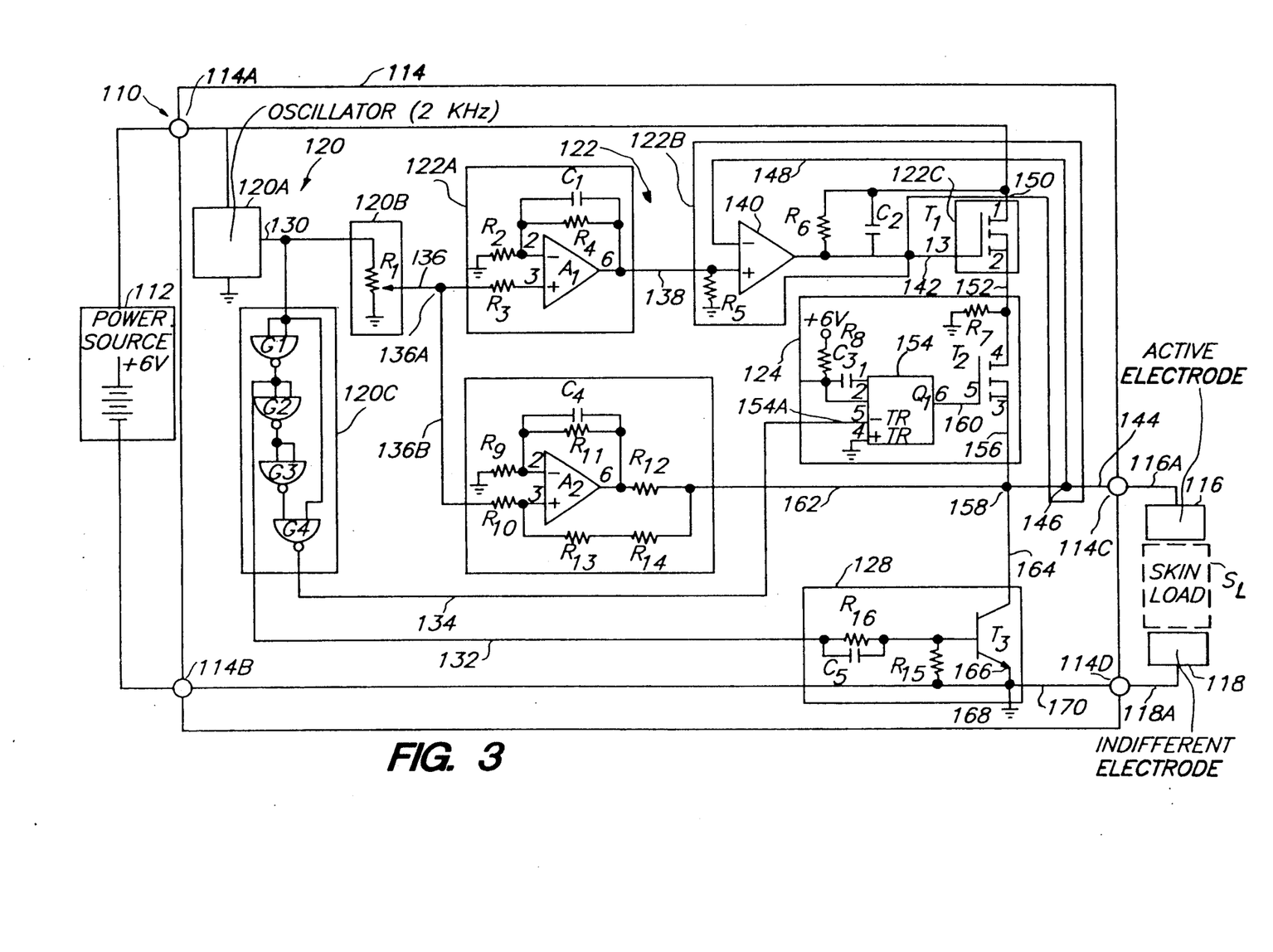
FIG. 3 is a circuit diagram to illustrate a more detailed embodiment of the invention for providing dual-segment, voltage-plus-current, therapeutic pulses, such embodiment also having a sensor-feedback means for sensing an electrode potential during application of each pulse, such sensor-feedback means including means for feedback of a signal representative of the potential sensed and for controlling the pulse waveform as a function of the feedback signal.
Figure 4:
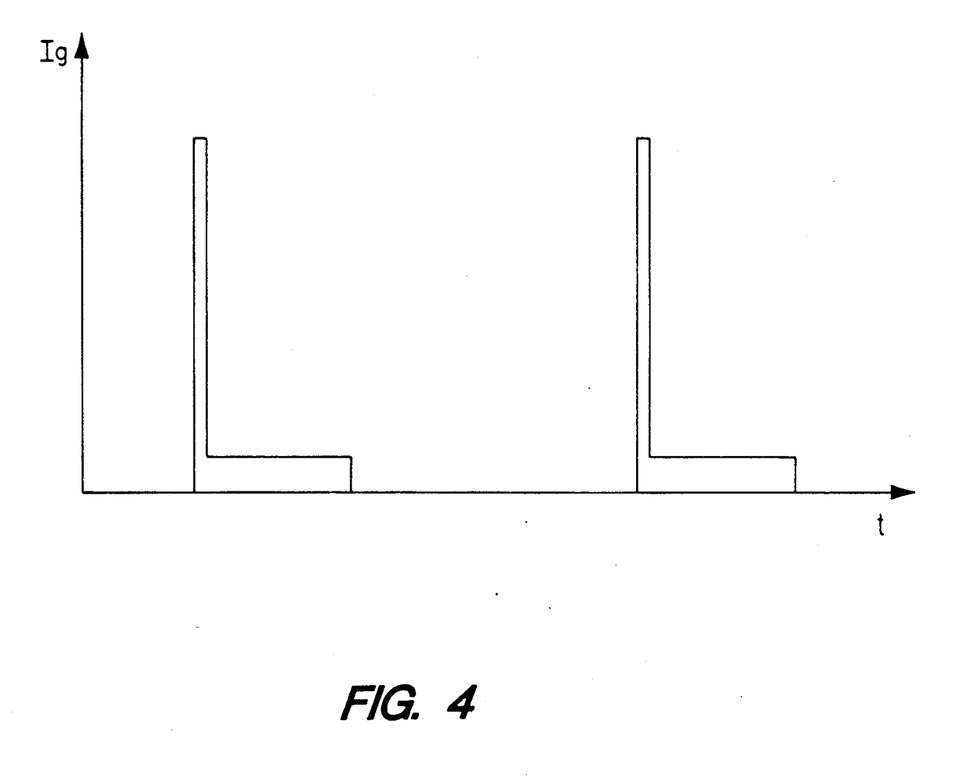
FIG. 4 is a graph showing an exemplary cycle period comprising a first generated current pulse having a first pulse segment and a second pulse segment, a second generated current pulse, and a pulse interval therebetween.

In FIG. 3, a circuit diagram representation of a further preferred embodiment of the invention is indicated generally at 110, illustrating an apparatus for providing dual-segment, voltage-plus-current, therapeutic pulses. Apparatus 110 includes a sensor-feedback means for sensing an electrode potential during application of each pulse, such sensor-feedback means including means for feedback of a signal representative of the potential sensed and for controlling the pulse waveform as a function of the feedback signal.

Apparatus 110 comprises an electric power source 112, a pulse generator means 114 for generating a train of periodic, dual-segment, voltage-plus-current, therapeutic pulses according to the present invention, an active electrode 116 having an ionic drug to be delivered, and an indifferent electrode 118. Power source 112 comprises a conventional, light-weight, button-type, dry element battery having a 6 volt potential. Electrodes 116 and 118 are of conventional design shown in electrical contact with skin tissue represented as a dashed-line block diagram as skin load $S_L$. Pulse generator means 114 further comprises input terminals 114a and 114b for electrically coupling to power source 112 to energize pulse generator means 114, and output terminals 114c and 114d for electrically coupling to electrodes 116 and 118 to deliver iontophoretic current to skin load $S_L$ via electrode leads 116a and 118a respectively.

A preferred embodiment of pulse generating circuitry suitable for generating a desired dual-segment, voltage-plus-current, therapeutic pulse is illustrated generally in FIG. 3 as pulse generator means 114. Pulse generator means 114 further comprises oscillator circuit 120, sensor-feedback circuit 122, voltage gate circuit 124, current source circuit 126, and discharge circuit 128. Pulse generator means 114 provides a train of therapeutic pulses having a predetermined frequency of 2 KHz. Each pulse has a controlled duration which defines a pulse width. Each pulse is separated from a subsequent pulse by an intervening pulse interval, the summation of each pulse width and subsequent pulse interval comprising a cycle period of approximately 500 microseconds. The duration of each pulse width and subsequent pulse interval are controlled to be approximately equal, such that a pulse width comprises approximately 50% of each cycle period. In other words, each cycle period generated by pulse generator means 114 is comprised of a pulse width extending over a first interval of time of approximately 250 microseconds, and a subsequent pulse interval extends over a second interval of time of approximately 250 microseconds, thereby defining a 50% duty cycle.

Each therapeutic pulse generated by pulse generator means 114 is further comprised of two pulse segments having a controlled duration and amplitude. Each dual-segment, therapeutic pulse is comprised of a first pulse segment extending over a predetermined first portion of the pulse width and having a predetermined average voltage amplitude, and a second pulse segment extending over a subsequent second portion comprising the remainder of the pulse width and having a predetermined average current amplitude.

Pulse generator means 114 includes means for generating a first pulse segment comprising a voltage output having a substantially constant 6 volt amplitude and a duration which can be varied as desired by the user, as more fully described below. Such first pulse segment generator means includes oscillator circuit 120, sensor-feedback circuit 122 and voltage gate circuit 124, which cooperate to generate the first pulse segment such that it commences at the onset of each therapeutic pulse and ends when a potential sensed at electrode 116 exceeds a predetermined threshold potential. This threshold potential may be controllably varied during operation as desired by the user, as more fully described below.

Pulse generator means 114 includes means for generating a second pulse segment comprising a current output having a substantially constant amplitude which may be controllably varied during operation as desired by the user, as more fully described below. Such second pulse segment generator means includes oscillator circuit 120 and current source circuit 126, which cooperate to generate the second pulse segment commencing at the onset of each pulse and extending throughout the duration of the pulse width, such that it is co-extensive with the entirety of the first pulse segment.

The dual-segment, therapeutic pulse thus generated by pulse generator means 114 is comprised of a first pulse segment corresponding to a substantially constant voltage output extending over an initial portion of the pulse width as controlled by the sensor-feedback circuitry, and a second pulse segment corresponding to a substantially constant current output which is superimposed upon the voltage output and extends over the entire pulse width.

Oscillator circuit 120 is comprised of an oscillator 120a, an amplitude control circuit 120b, and a one-shot array circuit 120c. Oscillator 120a is a conventional pulse generating device adapted to generate square-wave, voltage pulses at a 2 KHz frequency and an amplitude ranging between 0 and 6 volts. The oscillating output of oscillator 120a is coupled along a line 130 to amplitude control circuit 120b and one-shot array circuit 120c. Amplitude control circuit 120b, comprised of variable resistor R1, adjustably varies the amplitude of the oscillating output of oscillator 120a to provide a desired pulsed voltage output along a line 136 to drive sensor-feedback circuit 122 and current source circuit 126, thereby establishing a desired threshold potential which determines the predetermined average voltage amplitude for the first pulse segment and establishing a desired average current amplitude for the second pulse segment. One-shot array circuit 120c comprises an array of 4 digital gates G1, G2, G3 and G4, which are arranged to provide leading edge detection corresponding to selected positive-going or negative-going changes in the 25 output of oscillator 120a. In particular, an output is coupled from gate G1 along a line 132 to discharge circuit 128 thereby enabling depolarization to occur between electrodes 116 and 118 during each pulse interval in a known manner. In addition, an output is coupled from gate G4 along a line 134 to voltage gate circuit 124 thereby enabling a first pulse segment comprising a voltage output to be coupled across electrodes 116 and 118 only during a therapeutic pulse.

Sensor-feedback circuit 122 is comprised of a threshold reference circuit 122a, a feedback-compare circuit 122b, and a feedback-control circuit 122c. Threshold reference circuit 122a is comprised of an operational amplifier A1, which is configured with resistors R2, R3 and R4 and capacitor C1 to operate as a buffer amplifier to provide a pulsed voltage output along a line 138 to feedback-compare circuit 122b, such output comprising the desired threshold potential which determines the predetermined average voltage amplitude for the pulsed voltage output of the first pulse segment. The potential of the output of threshold reference circuit 122a is a function of the adjusted amplitude of the output of amplitude control circuit 120b, which adjusted output is coupled along line 136 to the non-inverting terminal of amplifier A1, and thus can be varied by the user as desired.

Feedback-compare circuit 122b, comprised of a comparator 140 which is configured with resistors R5 and R6, and capacitor C2, compares a first potential presented at the non-inverting terminal of comparator 140, which first potential comprises the threshold potential coupled along line 138, with a second potential presented at the inverting terminal of comparator 140, which second potential corresponds to a potential sensed at the active electrode 116 during each first pulse segment. Comparator 140 provides a comparator output along a line 142 to feedback-control circuit 122c as a function of such comparison. Feedback-compare circuit 122b includes a sensor-feedback means for sensing a potential at active electrode 116 during each first pulse segment and for feedback of the sensed potential to the inverting terminal of comparator 140. A potential at active electrode 116 is coupled along electrode lead 116a to output terminal 114c, and is further coupled along a line 144 to a feedback node 146. The sensor-feedback means of feedback-compare circuit 122b thus comprises a line 148 which couples a potential at feedback node 146, corresponding to a potential at active electrode 116, back to the inverting terminal of comparator 140.

Feedback-control circuit 122c is comprised of an enhancement-type MOSFET T1. The drain terminal of MOSFET T1 is coupled to the supply voltage along a line 150 to the positive terminal of power source 112. The source terminal of MOSFET T1 is coupled along a line 152 to voltage gate circuit 124. Output from comparator 140 is coupled along line 142, which output provides bias to the gate of MOSFET T1. MOSFET T1 functions in conjunction with voltage gate circuit 124 to selectively gate the supply voltage across the output terminals 114c and 114d and through skin load $S_L$, such that a first pulse segment, which is generated only during a first portion of each therapeutic pulse, has a controlled duration and voltage amplitude. Upon presentation of a positive-going, voltage pulse from oscillator 120a which corresponds to the onset of a therapeutic pulse, for example, the potential sensed and fed back to comparator 140 will generally comprise a lower potential than the threshold potential being compared against, thereby producing a comparator output having a high output state which will bias MOSFET T1 on. MOSFET T1 will thus continue to gate the supply voltage to voltage gate circuit 124 during the initial portion of each therapeutic pulse until the output from comparator 140 assumes a low output state causing MOSFET T1 to become biased off, which event will occur when the potential at the active electrode 116 exceeds the threshold potential.

Voltage gate circuit 124 is comprised of digital gate 154, resistors R7 and R8, capacitor C3, and enhancement-type MOSFET T2. The drain terminal of MOSFET T2 is coupled to the voltage output of feedback-control circuit 122c by line 152. The source terminal of MOSFET T2 is coupled along a line 156 to an output node 158. Output node 158 electrically interconnects with line 144 to couple the voltage output of MOSFET T2 across output terminals 114c and 114d. Output from gate G4 of one-shot array circuit 120c is coupled along line 134 to the negative trigger input terminal 154a of gate 154. Output from gate 154 is coupled along a line 160, which output provides bias to the gate of MOSFET T2. Almost immediately following a positive-going, voltage pulse from oscillator 120a which corresponds to the onset of a therapeutic pulse, for example, a leading edge of a negative-going, voltage pulse produced by gate G4 along line 134 will trigger a positive-going pulsed voltage output from gate 154 thereby biasing MOSFET T2 on. MOSFET T2 becomes biased off between therapeutic pulses.

Thus, while MOSFET T1 and MOSFET T2 both remain biased on, the supply voltage will be fully coupled across the output terminals 114c and 114d, thereby producing a voltage output comprising the first pulse segment having a controlled duration and voltage amplitude. The predetermined average voltage amplitude of the first pulse segment is thus a function of the supply voltage. The predetermined first portion of each pulse width over which the first pulse segment extends is a function of the threshold potential selected. While the duration of the first pulse segment can be easily regulated by simple timing circuitry, it is considered preferable to do so using a sensor-feedback approach, such as sensor-feedback circuit 122 of the present embodiment. To the extent that the polarization capacity of the skin load $S_L$ being charged during the first pulse segment may vary from patient to patient, sensor-feedback circuit 122 automatically accommodates such variation by controlling the duration of such voltage pulse as a function of a feedback potential sensed across the load. Sensor-feedback circuit 122 thus automatically varies the duration of the first pulse segment as needed to meet the particular electrical characteristics of the patient's skin. Sensor-feedback circuit also prevents the skin being treated from being subjected to unsafe voltage levels which could produce burns or shocks. The amplitude of the applied voltage is limited by the battery potential, for example, and the potential generated across the skin load $S_L$ during each first pulse segment is limited by the selected threshold potential.

Current source circuit 126 is comprised of operational amplifier A2, which is configured with resistors R9, R10, R11, R12, R13 and R14, and capacitor C4, to function as a constant current source which provides a pulsed current output along a line 162 to output node 158. Output node 158 electrically interconnects with line 144 to couple the pulsed current output of current source circuit 126 to output terminals 114c and 114d. A node 136a electrically interconnects with line 136 to couple the pulsed voltage output from amplitude control circuit 120b along a line 136b to the non-inverting terminal of amplifier A2. Upon presentation of a positive-going, voltage pulse from oscillator 120a which corresponds to the onset of a therapeutic pulse, for example, a pulsed voltage output from amplitude control circuit 120b having a desired amplitude is presented to current source circuit 126. Current source circuit 126 provides a pulsed current output having a constant current amplitude which is a function of the adjusted voltage amplitude of amplitude control circuit 120b and the voltage-to-current transfer function of current source circuit 126. It is preferred that the current amplitude remain substantially constant throughout the second pulse segment since the iontophoretic current delivered is directly proportional to the rate of ion migration. Oscillator circuit 120 and current source circuit 126 thus cooperate to generate a second pulse segment having a predetermined average current amplitude which can be controllably varied as desired, such that ionic drug is administered at a controlled rate.

Pulse generator means 114 thus generates the second pulse segment throughout the duration of each therapeutic pulse, such that the pulsed current output comprising the second pulse segment is co-extensive with the entirety of the pulsed voltage output comprising the first pulse segment.

Pulse generator means 114 can, however, generate the second pulse segment such that it is co-extensive with all, some or none of the first pulse segment, provided that at least some part of the second pulse segment, which constitutes the subsequent second portion of the pulse width, follows the first pulse segment. Pulse generator means 114 can include means for interactively controlling the generation of the first pulse segment and the second pulse segment, such that the second pulse segment is generated in the desired time relation with respect to the first pulse segment. If desired, for example, current source circuit 126 can further comprise a gate disposed along line 136b which selectively couples pulsed voltage output from oscillator circuit 120 to current source circuit 126, wherein gate bias is controlled as a function of the output from comparator 140, such that output from current source circuit 126 commences immediately following completion of the voltage pulse comprising the first pulse segment.

Discharge circuit 128, comprising bipolar transistor T3, which is configured with resistors R15 and R16, and capacitor C5, function as a means for discharging or depolarizing an unwanted potential which can develop during each therapeutic pulse across the electrodes 116 and 118 and skin load $S_L$ disposed therebetween. The collector terminal of transistor T3 is coupled along a line 164 to output node 158 which interconnects with active electrode 116 via line 144, output terminal 114c and electrode lead 116a. The emitter terminal of transistor T3 is coupled along a line 166 to a ground node 168 which electrically interconnects with indifferent electrode 118 via a line 170 coupling ground node 168 to output terminal 114d and electrode lead 118a. Output from gate G1 is coupled along line 132, which provides bias to the base terminal of transistor T3, such that transistor T3 as s switch which is in an "on" state to enable discharge therethrough during each pulse interval and in an "off" state during each pulse width.

Suitable circuit components for the circuit depicted in FIG. 3 are listed in Table 1 below, wherein reference is made to standard identification code numbers. However, it should be understood that these values are illustrative only and a variety of available components can be selected which are functionally equivalent thereto.

TABLE 1

| Ref. No. | Ident. Code |
| --- | --- |
| G1 through G4 | CD 4093 BF |
| A1 | Op 17 EZ |
| A2 | OP 42 EZ |
| T1 and T2 | CD 4066 BCN |
| T3 | 2N 2222 |
| 140 | PM 219 Y |
| 154 | CD 4098 BE |
| R1 | 10K ohms |
| R2 | 5.1K ohms |
| R3 | 11K ohms |
| R4 | 11K ohms |
| R5 | 100K ohms |
| R6 | 1K ohms |
| R7 | 47K ohms |
| R8 | 39K ohms |
| R9 | 100K ohms |
| R10 | 100K ohms |
| R11 | 10K ohms |
| R12 | 100 ohms |
| R13 | 9.1K ohms |
| R14 | 820 ohms |
| R15 | 1K ohms |
| R16 | 7.33K ohms |
| C1 | 18 pf |
| C2 | 1500 pf |
| C3 | 680 pf |
| C4 | 10 pf |
| C5 | 270 pf |

While the invention has been described above in connection with the particular embodiments and examples, one skilled in the art will appreciate that the invention is not necessarily so limited and that numerous other embodiments, examples, uses and modifications of and departures from the embodiments, examples and uses disclosed may be made without departing from the inventive concepts.

What is claimed is:

1. In a method of pulsed iontophoretic drug therapy, of the type wherein periodic electrical pulses are generated and applied to drive an active electrode and an indifferent electrode of an iontophoresis device in contact with the skin of a living body to deliver drug therethrough, an improvement comprising:

generating a train of said periodic pulses at a predetermined frequency, each pulse thereof extending over a first interval of time which defines a predetermined pulse width of said pulse, each pulse thereof being separated from a subsequent pulse by a second interval of time which defines a pulse interval which immediately follows said pulse width, the summation of said pulse width and immediately following pulse interval comprising a cycle period which is the reciprocal of said frequency, wherein each pulse has waveform characteristics, comprising:

a first pulse segment extending over a predetermined first portion of said pulse width and having a predetermined first average current amplitude; and a second pulse segment extending over a subsequent second portion comprising the remainder of said pulse width and having a predetermined second average current amplitude;

wherein said first average current amplitude is greater than said second average current amplitude and said second average current amplitude is greater than an average current amplitude during the pulse interval; and wherein said first portion comprises not more than 50% of said pulse width.

2. The method of claim 1, wherein said pulse width comprises between 10% and 80% of said cycle period.

3. The method of claim 2, wherein said frequency of said pulses is between 0.5 and 50 kkilohertz.

4. The method of claim 3, wherein said first average current amplitude is between 0.1 and 50 milliamperes, and said second average current amplitude is between 0.01 and 5 milliamperes.

5. In a method of pulsed iontophoretic drug therapy, of the type wherein periodic electrical pulses are generated and applied to drive an active electrode and an indifferent electrode of an iontophoresis device in contact with the skin of a living body to deliver drug therethrough, an improvement comprising:

generating a train of said periodic pulses at a predetermined frequency, each pulse thereof extending over a first interval of time which defines a predetermined pulse width of said pulse, each pulse thereof being separated from a subsequent pulse by a second interval of time which defines a pulse interval which immediately follows said pulse width, the following pulse interval comprising a cycle period which is the reciprocal of said frequency, wherein each pulse has waveform characteristics, comprising:

a first pulse segment extending over a predetermined first portion of said pulse width and having a predetermined average voltage amplitude; and a second pulse segment extending over a subsequent second portion comprising the pulse width and having a predetermined average current amplitude greater than an average current amplitude during the pulse interval;

wherein said first portion comprises not more than 50% of said pulse width.

6. The method of claim 5, wherein said pulse width comprises between 10% and 80% of said cycle period.

7. The method of claim 6, wherein said frequency of said pulses is between 0.5 and 50 kilohertz.

8. The method of claim 7, wherein said average voltage amplitude is between 3 and 25 volts, and said average current amplitude is between 0.01 and 5 milliamperes.

9. In an apparatus for applying pulsed iontophoretic drug therapy to a living body, of the type having an electric power source, an active electrode and an indifferent electrode adapted to contact the skin of a living body, and a pulse generator means coupled to said power source and said active electrode and said indifferent electrode, said pulse generator means for generating a train of periodic electrical pulses and for applying said train of pulses to drive said electrodes to conduct a net DC current through said skin, an improvement comprising:

a pulse generator means for generating a train of periodic pulses at a predetermined frequency, each pulse thereof extending over a first interval of time which defines a predetermined pulse width of said pulse, each pulse thereof being separated from a subsequent pulse by a second interval of time which defines a pulse interval which immediately follows said pulse width, the summation of said pulse width and immediately following pulse interval comprising a cycle period which is the reciprocal of said frequency, said pulse generator means further comprising:

a first pulse segment generator means for generating a first pulse segment extending over a predetermined first portion of said pulse width and having a predetermined first average current amplitude; and a second pulse segment generator means for generating a second pulse segment extending over a subsequent second portion comprising the remainder of said pulse width and having a predetermined second average current amplitude a discharge means providing an average current amplitude during the pulse interval that is less than the second average current amplitude;

wherein said first average current amplitude is greater than said second average current amplitude; and wherein said first portion comprises not more than 50% of said pulse width.

10. The apparatus of claim 9, wherein said pulse width comprises between 10% and 80% of said cycle period.

11. The apparatus of claim 10, wherein said frequency of said pulses is between 0.5 and 50 kilohertz.

12. The apparatus of claim 11, wherein said predetermined first average current amplitude is between 0.1 and 50 milliamperes, and said second average current amplitude is between 0.01 and 5 milliamperes.

13. In an apparatus for applying pulsed iontophoretic drug therapy to a living body, of the type having an electric power source, an active electrode and an indifferent electrode adapted to contact the skin of a living body, and a pulse generator means coupled to said power source and said active electrode and said indifferent electrode, said pulse generator means for generating a train of periodic electrical pulses and for applying said train of pulses to drive said electrodes to conduct a net DC current through said skin, an improvement comprising:

a pulse generator means for generating a train of periodic pulses at a predetermined frequency, each pulse thereof extending over a first interval of time which defines a predetermined pulse width of said pulse, each pulse thereof being separated from a subsequent pulse by a second interval of time which defines a pulse interval which immediately follows said pulse width, the summation of said pulse width and immediately following pulse interval comprising a cycle period which is the reciprocal of said frequency, said pulse generator means further comprising:

a first pulse segment generator means for generating a first pulse segment extending over a predetermined first portion of said pulse width and having a predetermined average voltage amplitude; and a second pulse segment generator means for generating a second pulse segment extending over a subsequent second portion comprising the remainder of said pulse width and having a predetermined average current amplitude greater than an average current amplitude during the pulse interval;

wherein said first portion comprises not more than 50% of said pulse width.

14. The apparatus of claim 13, wherein said pulse width comprises between 10% and 80% of said cycle period.

15. The apparatus of claim 14, wherein said frequency of said pulses is between 0.5 and 50 kilohertz.

16. The apparatus of claim 15, wherein said average voltage amplitude is between 3 and 25 volts, and said average current amplitude is between 0.01 and 5 milliamperes.

* * * * *